(12) United States Patent
Beck et al.

(10) Patent No.: US 7,494,484 B2
(45) Date of Patent: Feb. 24, 2009

(54) METHOD OF REMOVING PARTICULATE DEBRIS WITH AN INTERVENTIONAL DEVICE

(76) Inventors: Robert C. Beck, 2256 Hendon Ave., St. Paul, MN (US) 55108-1452; Hans Mische, 32 Highbanks Pl., St. Cloud, MN (US) 56301

( * ) Notice: Subject to any disclaimer, the term of this patent is extended or adjusted under 35 U.S.C. 154(b) by 0 days.

(21) Appl. No.: 09/995,303

(22) Filed: Nov. 27, 2001

(65) Prior Publication Data

US 2002/0068895 A1    Jun. 6, 2002

Related U.S. Application Data

(63) Continuation of application No. 09/459,225, filed on Dec. 10, 1999, now abandoned, and a continuation-in-part of application No. 09/637,529, filed on Aug. 11, 2000, now abandoned.

(51) Int. Cl.
*A61M 31/00*    (2006.01)

(52) U.S. Cl. .................................................. 604/509
(58) Field of Classification Search .............. 604/27, 604/30, 22, 264, 523, 246, 247, 500, 118, 604/508, 509
See application file for complete search history.

(56) References Cited

U.S. PATENT DOCUMENTS

| | | | | |
|---|---|---|---|---|
| 5,100,425 | A * | 3/1992 | Fischell et al. | 606/159 |
| 5,135,482 | A * | 8/1992 | Neracher | 604/22 |
| 5,250,060 | A * | 10/1993 | Carbo et al. | 606/159 |
| 5,462,529 | A * | 10/1995 | Simpson et al. | 604/101.04 |
| 6,080,170 | A * | 6/2000 | Nash et al. | 606/159 |
| 6,524,323 | B1 * | 2/2003 | Nash et al. | 606/159 |
| 6,592,567 | B1 * | 7/2003 | Levin et al. | 604/509 |
| 6,605,074 | B2 * | 8/2003 | Zadno-Azizi et al. | 604/509 |

* cited by examiner

*Primary Examiner*—Matthew F Desanto
(74) *Attorney, Agent, or Firm*—Beck & Tysver, P.L.L.C.

(57) ABSTRACT

The present invention relates to an interventional device for interacting with occlusive material. A wall attachment jet moves and removes particulate from lumens such as vessels.

14 Claims, 6 Drawing Sheets

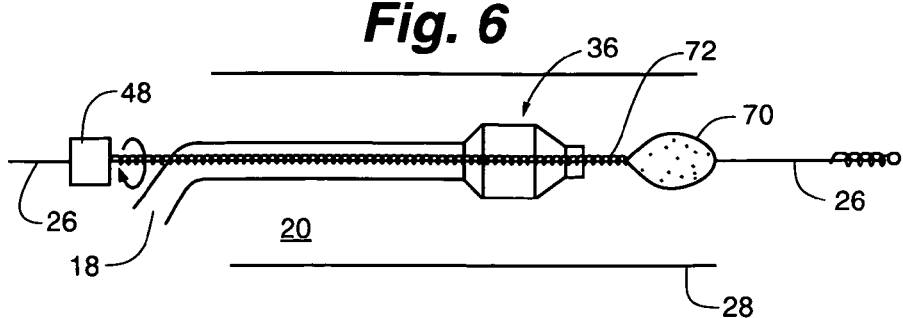
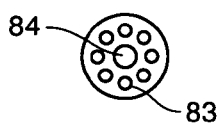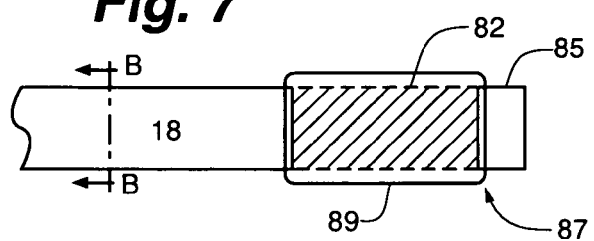
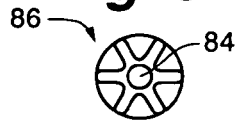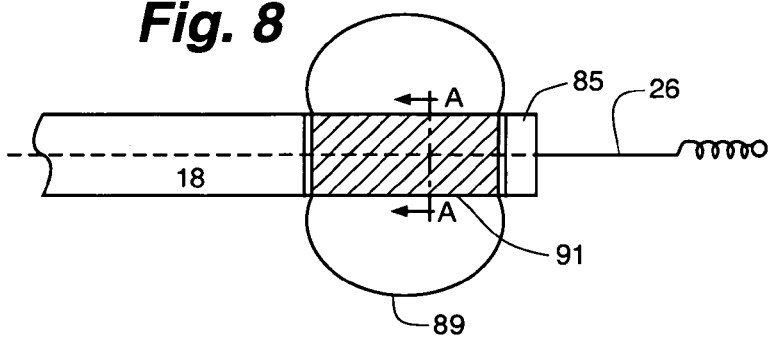
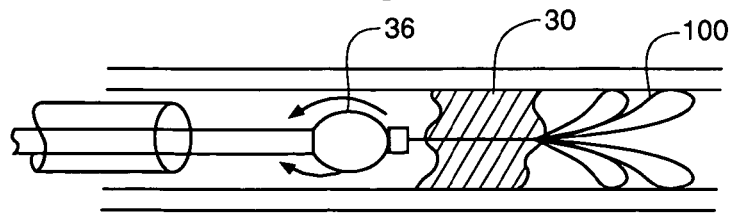

METHOD OF REMOVING PARTICULATE DEBRIS WITH AN INTERVENTIONAL DEVICE

CROSS REFERENCE TO RELATED APPLICATIONS

The present application is a Continuation of U.S. patent application Ser. No. 09/459,225 filed Dec. 10, 1999 now abandoned.

The present application is a Continuation in Part of U.S. patent application Ser. No. 09/637,529 filed Aug. 11, 2000.

Each application is incorporated in its entirety.

FIELD OF THE INVENTION

The invention relates generally to an interventional device, and more particularly to a device that utilizes the energy in a pressurized fluid to remove occlusive material from vessels or lumens in the body. The invention is disclosed in the context of the removal of blood thrombus.

BACKGROUND OF THE INVENTION

Catheters which are used to remove occlusive material from lumens within the body are well known. They range from simple aspiration devices to complex high energy devices Occlusive materials such as plaque, atheroma, and emboli vary in their mechanical properties and various energy sources have been proposed to break up occlusive material. These proposals include the use of high energy fluid jets or the circulation of abrasive slurry within the vessel. The use of mechanical impellers and/or blades has been proposed and clinical work has been performed with a "rotorblader" device.

Laser light energy and either ultrasonic or acoustic energy have been proposed to breakdown occlusive material. The use of radio frequency electromagnetic energy has been proposed as well.

For example fluid pressure thrombectomy systems are known from U.S. Pat. No. 4,690,672 to Veltrup among others. In the Veltrup device, a reward-facing jet entrains thrombus and blood from the patient, and ejects these into a secondary discharge lumen, which removes both thrombus and blood from the body.

Impeller based cutting devices are known from U.S. Pat. No. 4,729,763 among others. In this device the mechanically rotated blade interacts directly with the occlusive material.

Ultrasonic based devices are known from U.S. Pat. No. 5,368,557. In this device the ultrasonic energy is used to break up the occlusive material and a fluid is supplied to cool the ultrasonic tip.

SUMMARY OF THE INVENTION

In contrast to the jets of the prior art, the present invention relies on a substantially annular sheet jet which is "bent" and flows around a "nubbin". The asymmetries introduced by the nubbin results in flow which is deflected through an angle. This deflected jet is in the form of a vortex and it presents a large and energetic surface to entrain thrombus and other occlusive material. In operation the jet emerges from a generally annular gap or slot and attaches itself to a shoulder of the nubbin. As the jet emerges from the gap it spreads over the contour of the shoulder which gives the jet a greater working area. In some embodiments the jet ultimately enters a throat or lumen which provides good pressure recovery for the jet improving overall extraction efficiency. In some versions, the interventional device may be delivered over a guidewire. In some versions the interventional device may be used as a "guidewire" for the delivery of other devices.

In one embodiment the present invention teaches the use of a free standing deflected jet alone. In other embodiments the bent jet device is used in conjunction with a complimentary energy source. Typically the jet is used as an emulsifying pump to break up and transport occlusive material out of the body through an appropriate sheath or discharge lumen. In some versions, the catheter may be delivered over a guide wire or through a guide sheath. In some embodiments the guide sheath may form the discharge lumen.

In most embodiments the deflected fluid jet is a substantially annular sheet of fluid which becomes attached to a barrier or wall. This deflected jet sheds vortices that follow the wall for a distance as they exchange momentum with the surrounding material. Various wall contours for the nubbin are within the scope of the invention. The principle for this geometry is a requirement is that the nubbin exceed the cap diameter at some location. This fluid jet entrains ambient fluid on its outer surface and the combined stream is deflected through an angle which depends on the initial energy in the flow and the wall contour. In most of the embodiments shown the total deflection is about ninety degrees, wile the initial angle between the emerging jet and the nubbins is between about zero degrees and forty-five degrees.

Other total turning angles are contemplated as well. For example an embodiment is shown where the flow attaches to the nubbin and is extracted by flowing into a lumen with essentially the same diameter as the nubbin. In this instance the total turning angle is nearly 180 degrees. Since this deflected jet presents a large and energetic surface to entrain and emulsify occlusive material asymmetries in its flow can be used to steer the device while navigating it in the lumen. In a typical configuration the jet emerges from a generally annular gap which is approximately concentric with the body of the catheter however at least one embodiment has asymmetries in two dimensions. This jet is initially directed outwardly from the central axis of the body of the device in an approximately radial direction. After the flow attaches itself to a shoulder of the nubbin it follows the nubbin through angles of ninety degrees or more. As the jet emerges from the relatively small nozzle area it spreads rapidly over the contour of the nubbin which has a much greater area and consequently the kinetic energy of the combined flow drops off rapidly.

In alternate embodiments the deflected jet acts a pump to emulsify, propel and preferentially remove particulate occlusive material. Where complementary energy sources are combed with the device, energy sources include mechanical impellers, ultrasonic probes, radio frequency probes, and laser fiber systems.

BRIEF DESCRIPTION OF THE DRAWING

The drawings show illustrative embodiments of the thrombectomy catheter. Various modifications to these designs may be made without departing from the scope of the invention. Elements which carry identical reference numerals are similar structures.

FIG. 6 is a schematic diagram of the distal end of an alternate embodiment of the interventional device;

FIG. 7 is a schematic diagram of the distal end of an alternate embodiment of the interventional device;

FIG. 8 is a schematic diagram of the distal end of an alternate embodiment of the interventional device;

FIG. 9 is a schematic diagram of the distal end of an alternate embodiment of the interventional device;

DETAILED DESCRIPTION

Figure 1:
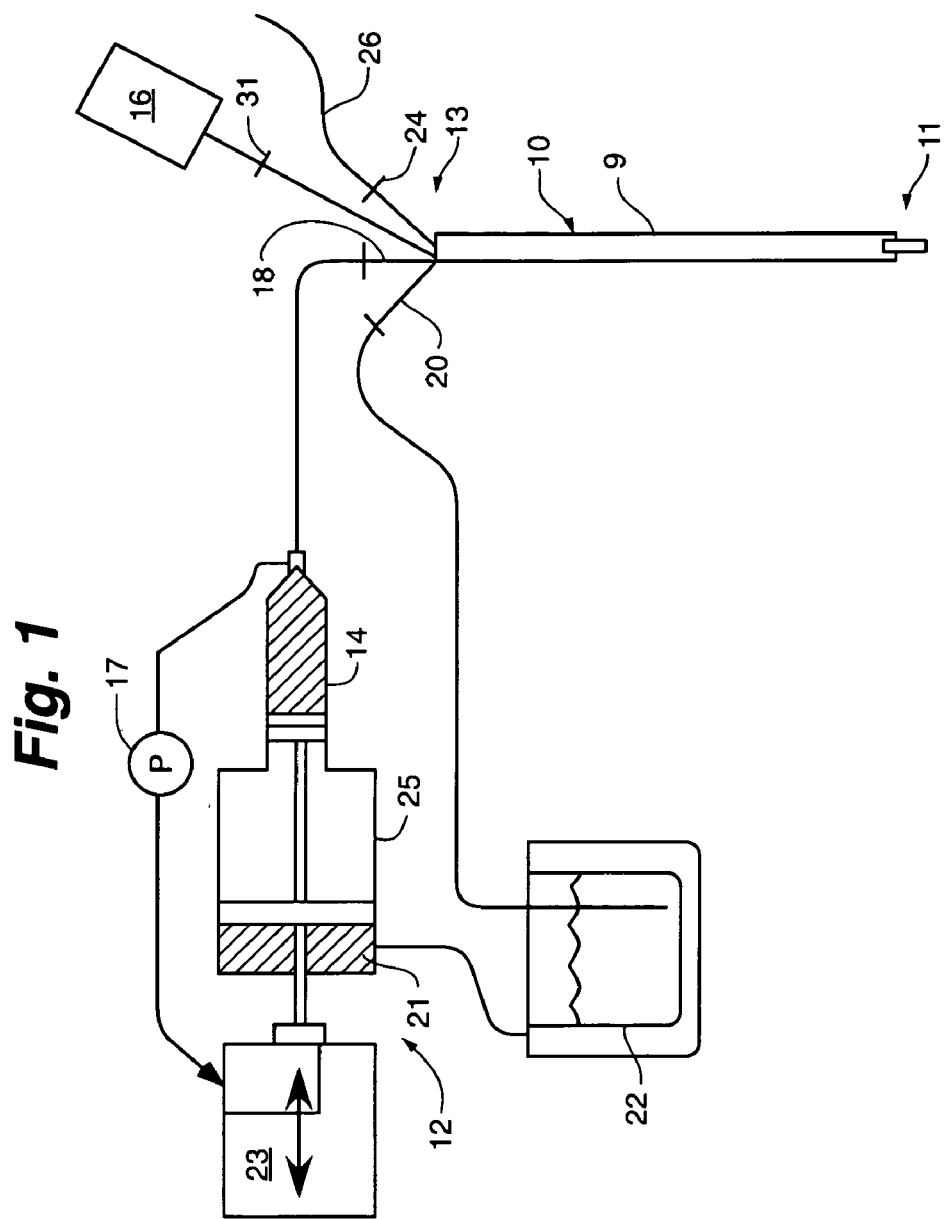
FIG. 1 is a system level diagram, showing the system in operation.

Turning to FIG. 1, the interventional device 10 is coupled to an injector 12. This interventional device 10 has a body 9 with a distal end 11 and a proximal end 13 and includes a high-pressure supply lumen 18. In this version there is a lower pressure discharge lumen 20 within the body 9. The high-pressure supply lumen 18 is located in the body as well and it is coupled to the injector 12 at the proximal end 13. In the figure the high pressure injector 12 supplies infusate which may be saline, thrombolytic fluid, contrast agent or the like, from a supply syringe 14. Throughout most of the drawings only the distal or "working" portion of the device is shown, as the details of length and construction are well known in this art.

The injector 12 may deliver infusate at a user selected delivery rate. In this mode the injector generates a corresponding pressure sufficient to induce the required flow. In an alternate mode of operation the injection pressure is specified and the flow rate varied to keep the pressure in bounds. In this mode a maximum discharge flow rate is set as a limit. The controller 23 may operate the syringe 14 under any of a number of user selected control programs. Typically, an overpressure sensor 17 is present on the injector 12 to shut the injector off if the high pressure supply line pressure exceeds a pre-set value. In some modes of operation pressure data from a pressure sensor 17 be used to control the delivery rate of the injector 12 through the operation of the controller 23.

In use, the distal end 11 of the interventional device catheter 10 interacts with the thrombus or other occlusive material and the energetic infusate fluid jet entrains both blood and thrombus from the patient, which are discharged through the lower pressure discharge lumen 20 to a collection container 22 or optionally to the vacuum side 21 of the collection syringe 25. In this instance it is preferable that the collection bag 22 is semi rigid to modulate the pressure applied to the discharge lumen 20. Preferably the collection syringe chamber 25 and the supply syringe chamber 14 may be combined into a unit with a single plunger for connection to the injector 12. This combination syringe permits close control over the relative volumes of injected fluid and extracted fluid.

The proximal end 13 of the interventional device 10 includes couplings for the high pressure first lumen 18, the low pressure discharge lumen 20, and a third connection 24 for a guidewire 26. Additional connections typified by connection 31 may be used to introduce energy from remote energy source 16 in "hybrid" interventional devices.

Figure 2:
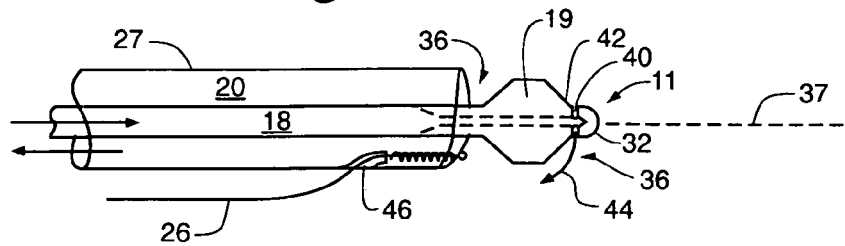
FIG. 2 is a schematic diagram of the distal end of the interventional device.

Turning to FIG. 2, there is shown a simple interventional device, which may be used to extract or simply macerate occlusive material. The device has a distal 11 end portion extending from the extraction sheath 27. The outer diameter of the interventional device catheter 10 is defined in this embodiment by the sheath 27 which also forms and defines one wall of a throat 36 with respect to a nubbin 19. The central axis 37 defined in the figure is used to describe flow directions. The high pressure supply lumen 18 delivers fluid to a slit 40 which discharges fluid in a generally radial direction with respect to the central axis 37. Typically the slit or gap 40 will have dimensions defining an orifice area much smaller than the cross-sectional dimension of the interior of the high pressure supply lumen 18. In the figure the slit or gap 40 initially directs the jet away from the central axis 37 at about ninety degrees but other angles are contemplated within the scope of the disclosure. A slight offset 42 may be formed proximate the flow body or nubbin 19. The height of the offset forms a step that helps to turn the sheet of fluid, which emerges, from the gap 40. As the fluid emerges, it entrains fluid on both sides of the jet. Since the amount of fluid which can be entrained on the inner side next to the nubbin 19 is limited by the asymmetrical relation between the cap 32 and the nubbin 19, the jet turns and follows the contour of the nubbin 19. In the figure this flow is seen by the curvature of the arrow 44 depicting fluid flow, turning through approximately ninety degrees in the illustrative example. This flow enters into the annular throat 36 formed between the sheath 27 and the nubbin 19 and may be extracted from the lumen 20. There is a wide tolerance for the dimensions of the elements. However good flow can usually be achieved by ensuring that the gap or slit is very narrow. Both lesser and greater degrees of turning are contemplated. Ninety degrees of turning is desirable because it presents more fluid entrainment area to engage and eject thrombus. The energy in the jet is greatest near the center of the axis 37 and drops off rapidly in the radial direction. This effect limits damage to the vessel walls when the device is used outside the protective sheath.

In this embodiment of the interventional device a guide wire 26 is shown which may be used to position the device 10 within a body lumen. For this embodiment the guide wire may be introduced into the discharge sheath 27 through an opening 46 which permits the interventional device to be delivered by the guidewire 26. It should also be noted, that the position of the aperture 46 is sufficiently proximal of the distal end of the sheath 27 to permit retraction of the guide wire 26 fully into the discharge lumen 20. On the other hand very short lumens do not "track" well and a typical device may have a guide wire lumen that is several centimeters long.

Figure 3:
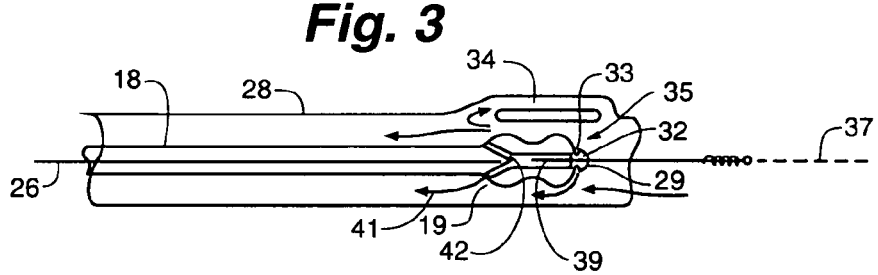
FIG. 3 is a schematic diagram of the distal end of an alternate embodiment of the interventional device.

FIG. 3 shows an illustrative second embodiment or design for the catheter 10. In this version of the device the gap 33 is formed as an annular ring at the junction between the cap 32 and the nubbin 19. Once again the jet is issued radially at an angle with respect to the central axis 37. In this version secondary jets 41 may be formed between the supply lumen and the discharge lumen to assist in removal of debris. These secondary jets 41 are supplied from the high pressure lumen 18 and a preferably formed as holes in the nubbin 19. In this version the high pressure supply lumen 18 delivers fluid to the plenum 39 which distributes the fluid to the annular ring jet gap 33. The control nubbin 19 forms a throat 35 with the sheath 28.

Although the slits in each embodiment differ in detail each preferably has a characteristic length, which is larger than the corresponding width. However due to manufacturing considerations rows of round holes may be substituted for the slit or gap 33 shown in the figures. It should also be noted that the complex body contours such as the bottle shape shown in FIG. 3 could be approximated by more easily manufactured conical sections. The primary source of asymmetry that causes the jet to attach to the body 9 is the difference in diameter between the cap 32 and the nubbin 19 maximum diameter.

Also in this version of the device the guide wire 26 exits the distal tip of the device concentric with the cap 32. Although not shown in detail for clarity the guide wire occupies a lumen that passes through the high pressure lumen 18. In this device a recirculation lumen 34 is supplied to maintain attachment of the jet to the nubbin 19 even when the distal opening of the device is occluded. In this embodiment essentially all the supply fluid in the high pressure lumen is ejected though the discharge lumen 20. Depending on the specific detail design of the surfaces, the total volume exhausted from the device is about 1.20 the supply fluid. It should be apparent that the device may move relative to the sheath. In FIG. 2 the device is "inside" the sheath while in FIG. 3 the device is inside the sheath. Using the sheath and the device together allows one to shred clot by advancing the device into clot and then removing it into the sheath.

Figure 4:
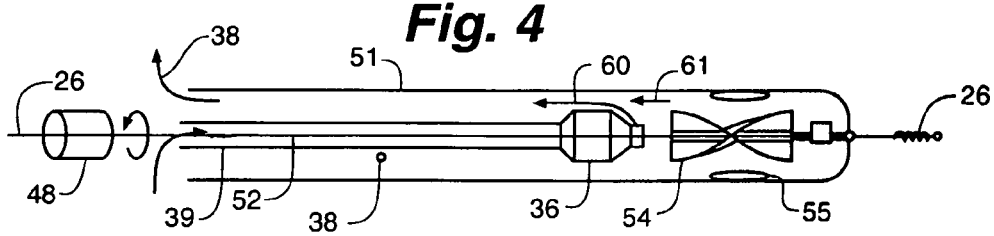
FIG. 4 is a schematic diagram of the distal end of an alternate embodiment of the interventional device.

FIG. 4 shows an illustrative alternate hybrid embodiment or design for the catheter assembly. In this version of the device an additional energy source is provided. In this version the air motor 48 drives a wire or flexible shaft 52 which spins a distal impeller 54. The impeller 54 sucks occlusive material into the sheath 51 through holes typified by hole 34 and emulsifies it. The end of the sheath 51 may be open or closed as seen in the figure. The jet pump 36 is formed by the body and cap combination, this pump 36 pumps the material out the discharge lumen 38 when supply fluid is introduced into the pump through supply lumen 39. The construction of the pump 36 follows the same principles set forth above for the direct interaction devices. In general, the deflected jet 60 entrains material macerated by the impeller shown as 61 and direct it to the exhaust lumen 38. The guidewire 26 may pass through the drive shaft 52 and extend from the distal end of the device.

Figure 5:
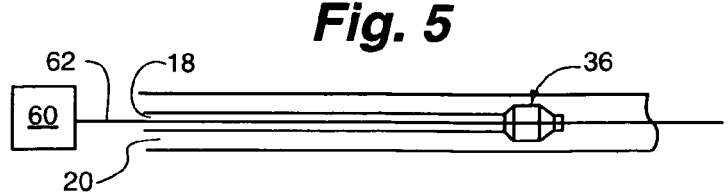
FIG. 5 is a schematic diagram of the distal end of an alternate embodiment of the interventional device.

FIG. 5 is a schematic of a hybrid device that uses a jet pump in combination with an energy source such as an ultrasonic horn 60. The ultrasonic energy is coupled to the wave-guide 62 which couples to the pump 36. In this embodiment the jet pump acts as a counter mass to radiate acoustic energy into the body. The wave guide may extend beyond the countermass forming a fixed guide wire for placing the device. High pressure fluid entering lumen 18 cools and constrains the wave guide so that more power can be coupled to the waveguide 62. The same construction can be used with other energy sources at other wavelengths. For example an optical fiber could be substituted for the acoustic wave-guide and the ultrasonic energy source replaced with a laser.

FIG. 6 is a schematic diagram of a hybrid device having rotating burr 70 driven by a remote air motor 48 through a drive shaft 72. The jet pump 36 is positioned near the burr to induce a flow over the burr to extract plaque and debris abraded from the treatment site. The discharge lumen 20 may be movable with respect to the burr and the burr may be movable with respect to the jet pump 36.

FIG. 7 is a schematic of a construction technique useful for making very small devices. The high pressure lumen terminates in a multilumen tube section 82, which in cross section has a central lumen 84 for accepting the passage of a guide wire. The radial holes typified by hole 83 accept fluid from the high pressure lumen and direct it to the cap 85. The fluid impinges on the cap and exits in a radial fashion from the gap 87. In this device the flow control body is an inflatable balloon 89 which is depicted in a closed state. One of the several radial lumens can be used as an inflation lumen for the balloon 89.

FIG. 8 is a schematic of an alternate construction with a balloon 89 as the flow control body and with a ribbed section 91 acting to direct fluid from the high pressure lumen 18 to the cap 85. In this version of the device the fluid exits in a twisting pattern because of the twist in the ribbed section 91. In the figure the balloon 89 is shown inflated forming the flow control body.

FIG. 9 shows a device, which incorporates a wire structure 100, which may be deployed from the guide wire lumen in the device. The wires trap large distal fragments of clot and their manipulation of the clot and help to cut it making it easier to emulsify with the jet devices 36. This structure may act as a filter as well as a dissecting wire. The wires may be made of nitinol and be used as a guidewire.

As seen in FIG. 9 the discharge sheath 27 is located in the vessel "V" partially blocking the vessel. As a consequence the blood in the vessel leak past the sheath 27 and flow out to ambient pressure through the discharge lumen 20.

Figure 10:
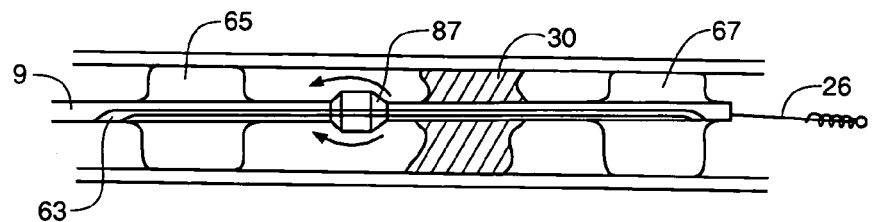
FIG. 10 is a schematic diagram of the distal end of an alternate embodiment of the interventional device.

FIG. 10 shows a catheter with one or two interventional balloons. As configured in the drawing the distal occlusion balloon 67 may be inflated to close off a treatment volume in a vessel. Inflation of the proximal angioplasty balloon 65 together with the inflation of the distal occlusion balloon isolates the clot and permits maceration without fear of circulation of debris. The perfusion lumen 63 connecting proximal of the proximal balloon and terminating distal of the distal balloon can be used to perfuse the tissues while maceration occurs. In this configuration the injector will be stopped occasionally and fluid aspirated form the gap 87. At the conclusion of the procedure a guide catheter or sheath may be advanced over the body 9 to aspirate the fluid from the space between the balloons as the distal or proximal balloon is deflated. In use this device can be used to clear clot from treatment areas where an angioplasty will be performed.

Figure 11:
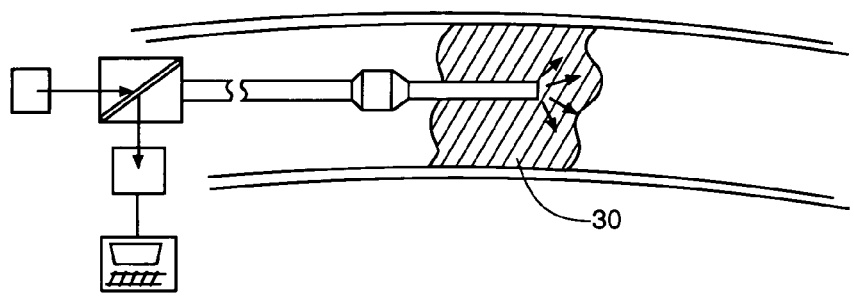
FIG. 11 is a schematic diagram of the distal end of an alternate embodiment of the interventional device.

FIG. 11 shows an optical fiber extending from the cap. The fiber is in occlusive material and the beam splitter and laser are used wit the detector and computer to monitors the spectra of the occlusive material.

Figure 12:
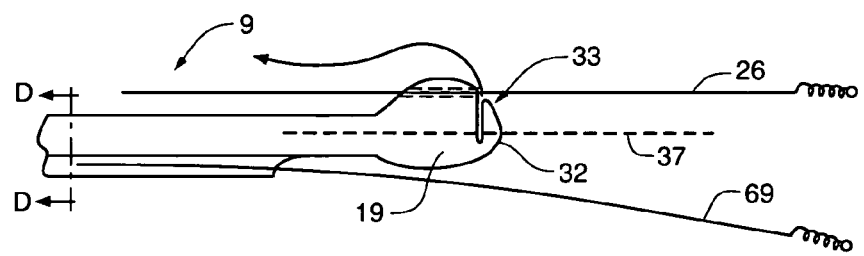
FIG. 12 is a schematic diagram of the distal end of an alternate embodiment of the interventional device.
Figure 12D:
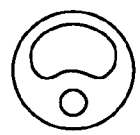

FIG. 12 shows an interventional device where the cap 32 and the nubbin 19 are made from a single piece of material. This construction allows a convention method of creating device which is asymmetric in two planes. In this version of the device the primary flow 80 attaches to the "upper" surface and spreads over the nubbin 19. The gap 33 is not radially symmetric in this version of the device. Two alternate guide wire locations are seen in the drawing. A guidewire 69 may occupy a companion lumen of the body 9. The guidewire 26 may occupy a lumen in the nubbin.

Figure 13:
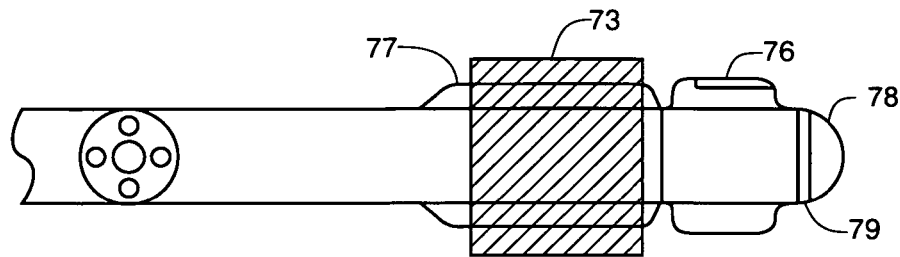
FIG. 13 is a schematic diagram of the distal end of an alternate embodiment of the interventional device.

FIG. 13 shows a low profile nubbin 76 mounted distal of a stent deployment balloon 77. In this configuration the nubbin may interact with the cap 78 to form a gap 79. Flow from the gap over the distal nubbin can be used to clear clot prior to stent placement.

Figure 14:
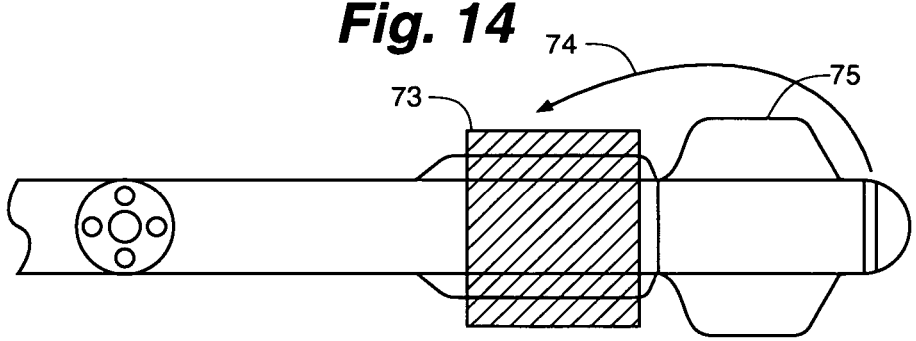
FIG. 14 is a schematic diagram of the distal end of an alternate embodiment of the interventional device.

FIG. 14 shows that the nubbin surface can be formed by an inflatable balloon 75 so that the flow 74 can be used to clear larger vessels or with lower energy. In this side by side dual balloon construction separate lumens in the multilumen shaft can be used to inflate the balloons separately.

Figure 15:
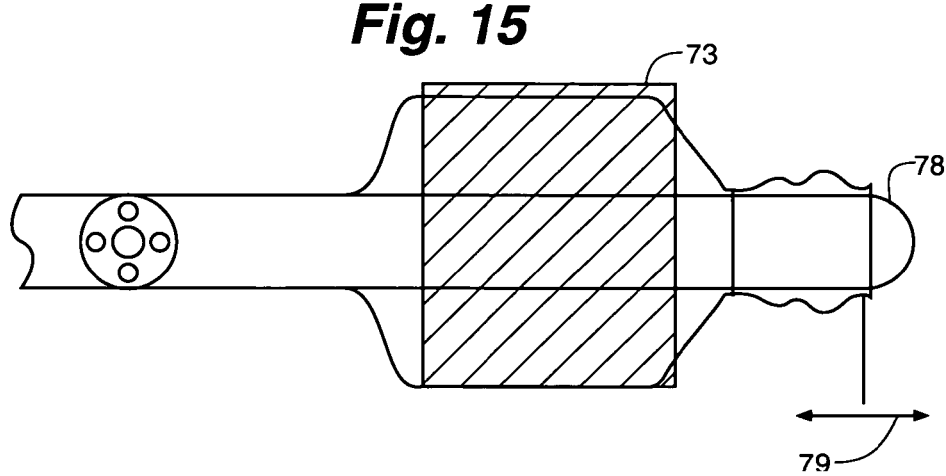
FIG. 15 is a schematic diagram of the distal end of an alternate embodiment of the interventional device.

FIG. 15 shows that once the clot is cleared the distal balloon can be collapsed and the stent deployment balloon can be inflated to place the stent 73. It may be preferable to retract the cap 78 along path 72 to close off flow and simultaneously pressurize one or more balloons with the internally diverted flow.

Figure 16:
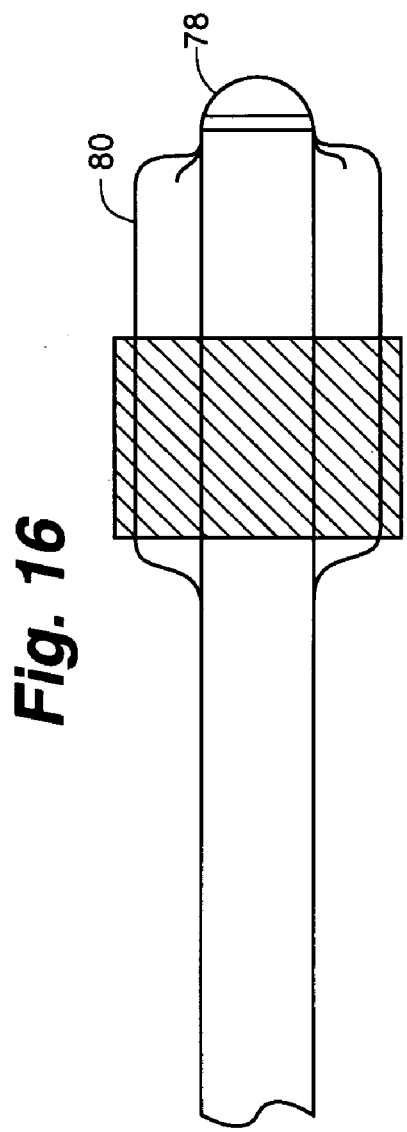
FIG. 16 is a schematic diagram of the distal end of an alternate embodiment of the interventional device; and, FIG. 17 is a schematic diagram of the distal end of an alternate embodiment of the interventional device.

FIG. 16 shows a single balloon 80 that can be inflated to multiple diameters thus permitting low profile entry and larger profile thrombolysis, and stent deployment.

Figure 17:
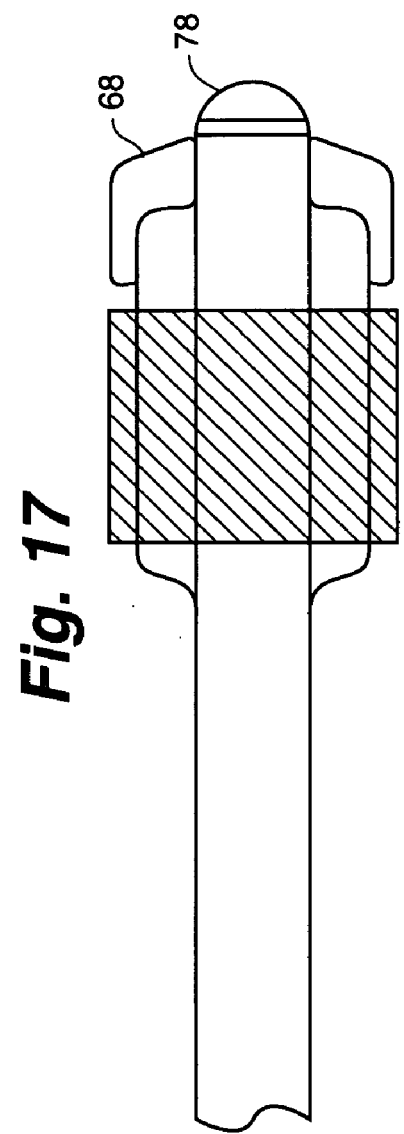

FIG. 17 shows a dual balloon structure where the balloons are shared. The secondary balloon 68 can be inflated before or after the primary balloon 80.

What is claimed is:

1. A method of removing particulate debris from a vessel using a catheter assembly the method comprising:
    inserting and advancing a sheath having a discharge lumen to a location in the vessel said delivery sheath discharge lumen coupled to a collection vessel, said sheath not having an occlusion balloon thereon such that said sheath partially blocks the vessel but allowing some blood flow in the vessel;
    inserting and advancing an interventional device to a treatment location said interventional device of type having;
    an elongate body enclosing a fluid supply lumen and an angioplasty therapy inflation lumen;
    said elongate body having a central axis extending in the direction of the therapy balloon;
    a gap communicating with said fluid supply lumen for introducing a primary fluid jet flow in said vessel, said gap located distal of a therapy balloon, said gap projecting said fluid jet in an initial direction away from the central axis of the interventional device; a tapered wall located immediately adjacent said gap, and forming an annular surface next to the gap on the interventional device;
    said wall serving to restrict entrainment of fluid by said primary fluid flow, thereby creating a pressure difference across said primary fluid jet flow such that said primary fluid flow turns through an angle away from said initial direction away from said wall and turns toward said wall thereby exhibiting the Coanda effect;
    delivering angioplasty treatment located near the distal tip of said elongate body;
    injecting a primary fluid; and
    promoting retrograde flow into said discharge lumen.

2. The method of claim 1 wherein said primary fluid is supplied by a supply syringe chamber.

3. The method of claim 2 wherein the fluid supplied is a thrombolytic.

4. The method of claim 2 wherein the fluid supplied is saline.

5. The method of claim 2 wherein the fluid supplied is contrast agent.

6. The method of claim 1 wherein said injection is carried out while moving said interventional device in said vessel with respect to said delivery sheath.

7. The method of claim 6 wherein said moving step begins near said occlusion and ends after the interventional device enters the delivery sheath.

8. The method of claim 1 wherein said fluid is injected at a first injection pressure above the blood pressure in the vessel and the injected fluid pressure drop to a second exhaust pressure in said delivery catheter where said exhaust pressure is above said blood pressure, establishing a pressure gradient in said discharge lumen and promoting flow from said gap to said discharge lumen.

9. The method of claim 1 wherein said discharge lumen is coupled to a syringe collection chamber.

10. The method of claim 1 wherein said discharge lumen is coupled to a syringe vacuum chamber.

11. The method of claim 1 wherein said primary fluid is supplied by a supply syringe chamber and said discharge lumen is coupled to a syringe vacuum chamber, and said supply syringe and vacuum syringe are operated together to couple fluid supply with discharge lumen collection.

12. A method of removing particulate debris from a vessel using a catheter assembly the method comprising:
    inserting and advancing a sheath having a discharge lumen to a location in the vessel said delivery sheath discharge lumen coupled to a collection vessel; said sheath not having an occlusion balloon thereon such that said sheath partially blocks the vessel but allowing some blood flow in the vessel;
    inserting and advancing an interventional device to a treatment location said interventional device of type having;
    an elongate body enclosing a fluid supply lumen and a stent delivery inflation lumen;
    a gap communicating with said fluid supply lumen for introducing a primary fluid flow in said vessel, said gap located distal of a stent deployment balloon, said gap projecting fluid in an initial direction away from the central axis of the interventional device; a tapered wall located immediately adjacent said gap; and forming an annular surface next to the gap on the interventional device;
    said wall serving to restrict entrainment of fluid by said primary fluid flow, thereby creating a pressure difference across said primary fluid flow such that said primary fluid flow turns through an angle away from said initial direction of the toward said wall thereby exhibiting the Coanda effect;
    delivering stent treatment located near the distal tip of said elongate body;
    injecting a primary fluid; and
    promoting retrograde flow into said discharge lumen.

13. The method of claim 12 further including a suction applied to said sheath lumen to withdraw material from said vessel.

14. The method of claim 13 further including a suction applied to said sheath lumen to withdraw material from said vessel.

* * * * *